(12) United States Patent
Satake (10) Patent No.: US 11,297,211 B2
(45) Date of Patent: Apr. 5, 2022

(54) ENDOSCOPE DISTAL END STRUCTURE AND ENDOSCOPE

(71) Applicant: OLYMPUS CORPORATION, Tokyo (JP)

(72) Inventor: Nau Satake, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/123,242

(22) Filed: Dec. 16, 2020

(65) Prior Publication Data

US 2021/0105386 A1 Apr. 8, 2021

Related U.S. Application Data

(63) Continuation of application No. PCT/JP2018/023530, filed on Jun. 20, 2018.

(51) Int. Cl.
*A61B 1/05* (2006.01)
*H04N 5/225* (2006.01)
*A61B 1/00* (2006.01)
*H04N 7/18* (2006.01)

(52) U.S. Cl.
CPC ....... *H04N 5/2253* (2013.01); *A61B 1/00009* (2013.01); *A61B 1/0011* (2013.01); *A61B 1/00114* (2013.01); *A61B 1/05* (2013.01); *H04N 7/183* (2013.01); *H04N 2005/2255* (2013.01)

(58) Field of Classification Search
CPC .. H04N 5/2253; H04N 7/183; A61B 1/00009; A61B 1/0011; A61B 1/00114; A61B 1/05

USPC ......................................................... 348/76
See application file for complete search history.

(56) References Cited

FOREIGN PATENT DOCUMENTS

| JP | H09-098944 A | 4/1997 |
|---|---|---|
| JP | 2001-128930 A | 5/2001 |
| JP | 2004-126533 A | 4/2004 |
| JP | 2015-039547 A | 3/2015 |
| JP | 2015-073537 A | 4/2015 |
| JP | 2015-73540 A | 4/2015 |
| JP | 2016-030027 A | 3/2016 |

OTHER PUBLICATIONS

International Search Report dated Sep. 18, 2018 issued in International Application No. PCT/JP2018/023530.

*Primary Examiner* — Nguyen T Truong
(74) *Attorney, Agent, or Firm* — Scully, Scott, Murphy & Presser, P.C.

(57) ABSTRACT

An endoscope distal end structure includes: an imaging module configured to generate an image signal and transmit the generated image signal using a cable; a frame having a through hole, the frame being configured to hold the imaging module with the imaging module being inserted into the through hole from an insertion port; a first adhesive that is arranged in a gap between an outer circumference of a proximal end part of a resin seal and an inner circumferential surface of the frame on a side of the insertion port; and a second adhesive that is arranged in a gap between the inner circumferential surface of the frame at a position in which the through hole is formed and the imaging module that is inserted into the through hole.

10 Claims, 10 Drawing Sheets

ENDOSCOPE DISTAL END STRUCTURE AND ENDOSCOPE

CROSS-REFERENCE TO RELATED APPLICATION

This application is a continuation of International Application No. PCT/JP2018/023530, filed on Jun. 20, 2018, the entire contents of which are incorporated herein by reference.

BACKGROUND

1. Technical Field

The disclosure relates to an endoscope distal end structure and an endoscope.

2. Related Art

In the related art, an endoscope inserts its elongated and flexible insertion portion with an imaging module provided at the distal end into a subject, such as a patient, thus acquires in-vivo image data of the subject using the imaging module that is arranged at the distal end part, and transmits the image data to an external information processing device. From a viewpoint of protection of the imaging device, the imaging module is inserted into a metal frame and an adhesive made of a thermosetting resin, or the like, is injected into the frame in order to reduce the stress applied to the imaging device and mitigate the effect of moisture, etc., on the imaging device (for example, refer to Japanese Laid-open Patent Publication No. 2001-128930).

SUMMARY

In some embodiments, an endoscope distal end structure includes: an imaging module configured to form an image of a subject using an optical unit, generate an image signal by performing photoelectric conversion on the formed image using an imaging device, and transmit the generated image signal using a cable; a frame that has a through hole penetrating in a direction of an optical axis of the optical unit, the frame being configured to hold the imaging module with the imaging module being inserted into the through hole from an insertion port that is formed in a proximal end part of the frame; a first adhesive that is arranged in a gap between an outer circumference of a proximal end part of a resin seal and an inner circumferential surface of the frame on a side of the insertion port to adhere at least part of the outer circumference of the proximal end part of the resin seal and at least part of the inner circumferential surface of the frame, the resin seal sealing at least from a proximal end of a side surface part of the optical unit to a joint of the cable; and a second adhesive that is arranged in a gap between the inner circumferential surface of the frame at a position in which the through hole is formed and the imaging module that is inserted into the through hole to adhere the frame and the imaging module to each other.

In some embodiments, an endoscope includes the endoscope distal end structure.

The above and other features, advantages and technical and industrial significance of this invention will be better understood by reading the following detailed description of presently preferred embodiments of the disclosure, when considered in connection with the accompanying drawings.

BRIEF DESCRIPTION

DETAILED DESCRIPTION

Endoscope distal end structures will be described as modes for carrying out the disclosure ("embodiments" below). The embodiments do not limit the disclosure. The embodiments do not limit the disclosure. Each drawing that is referred to in the following description only schematically represents shapes, sizes, and positional relationships to the extent that the content of the disclosure can be understood. In other words, the disclosure is not limited to only the shapes, the sizes and the positional relationship that are exemplified in each drawing. Furthermore, the drawings may contain components whose sizes and ratios differ among the drawings.

First Embodiment

Figure 1A:
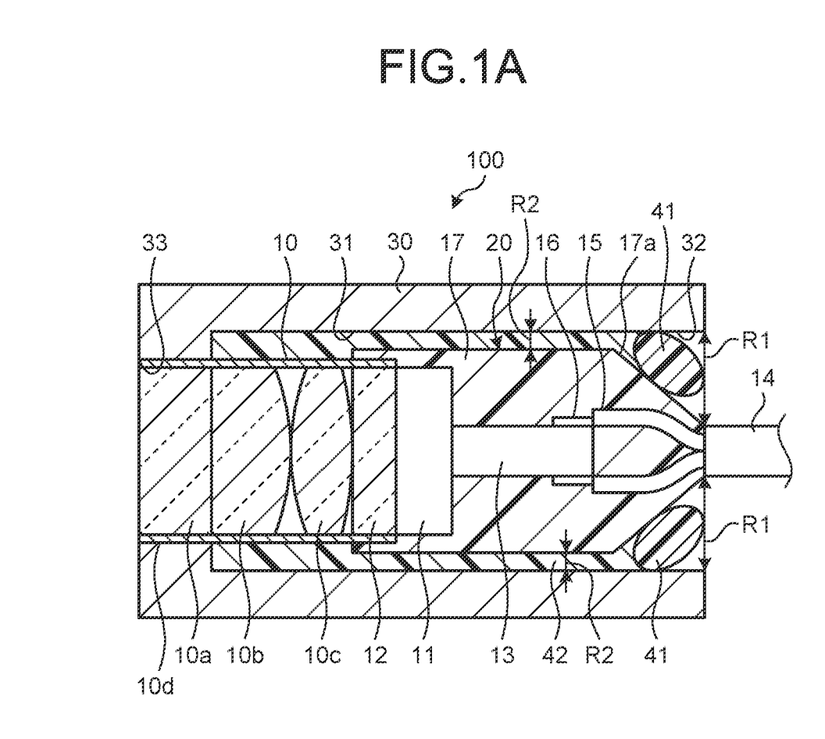
FIG. 1A is a cross-sectional view of an endoscope distal end structure according to a first embodiment of the disclosure and FIG. 1B is a back view of the endoscope distal end structure.
Figure 1B:
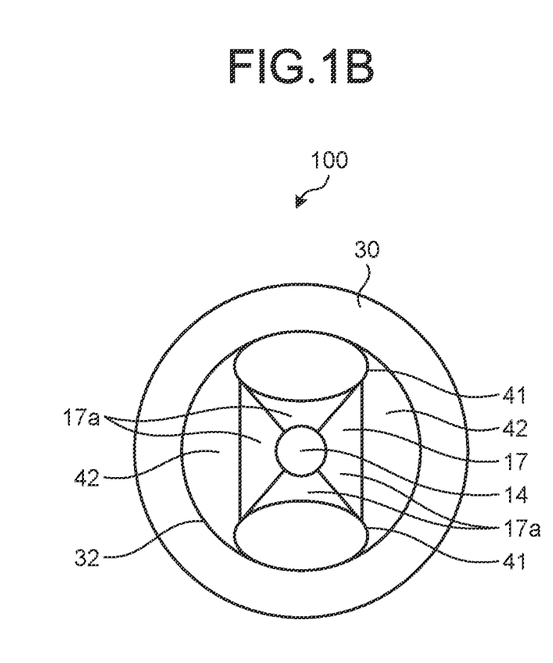
Figure 2:
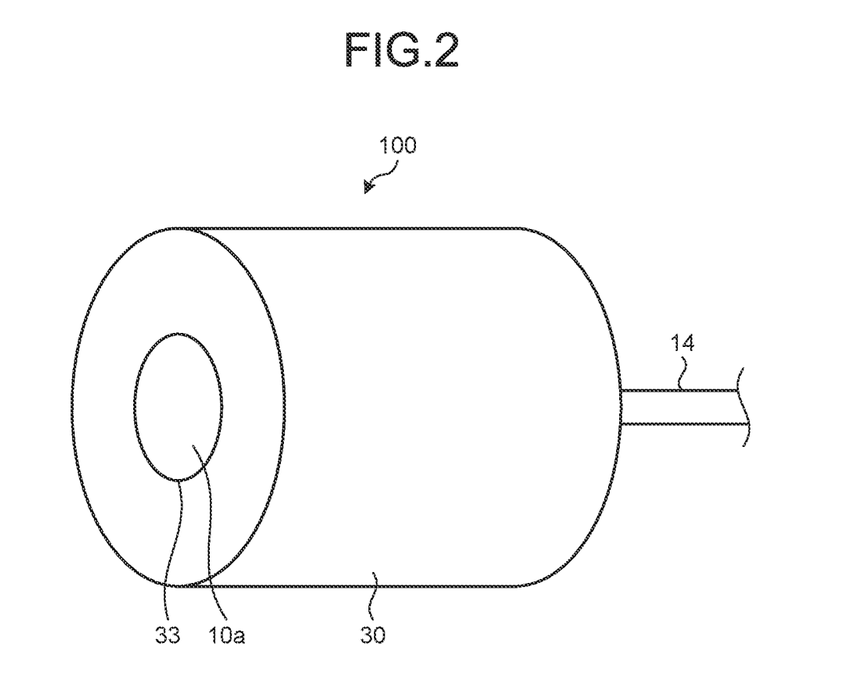
FIG. 2 is a perspective view of a frame that is used in the endoscope distal end structure in FIGS. 1A and 1B.

FIG. 1A is a cross-sectional view of an endoscope distal end structure 100 according to a first embodiment of the disclosure that is parallel to an optical-axis direction and FIG. 1B is a back view of the endoscope distal end structure 100. FIG. 2 is a perspective view of a frame that is used in the endoscope distal end structure in FIGS. 1A and 1B. The endoscope distal end structure 100 includes an imaging module 20, a frame 30, a first adhesive 41, and a second adhesive 42.

The imaging module 20 includes an optical unit 10 that forms an image of a subject, an imaging device 11 that performs photoelectric conversion on the image of the subject that is formed by the optical unit 10 and thus generates an image signal, a substrate 13 that is connected to a back surface of the imaging device 11, an assembly cable 14 including multiple signal cables 15 that are bundled and connected to the substrate 13, and a resin seal 17.

The optical unit 10 includes a plurality of objective lenses 10a, 10b and 10c and a lens holder 10d that holds a cover glass 12.

The imaging device 11 includes an image sensor such as a CCD and a CMOS and a light receiver of the imaging device 11 is covered with the cover glass 12 and is adhered. The imaging device 11 is held by the lens holder 10d with the cover glass 12 being adhered to the imaging device 11 and interposed in between.

The substrate 13 is electrically and mechanically connected to a connecting terminal that is formed on a back surface side of the imaging device 11 and that is not illustrated in the drawing. Cores 16 of the signal cables 15 that supply power to the imaging device 11 or input signals to the imaging device 11 or output signals from the imaging device 11 are connected onto the substrate 13.

The resin seal 17 seals from a proximal end side of a side surface part of the optical unit 10 to an end part of the assembly cable 14 from which the signal cables 15 are drawn. The resin seal 17 protects the imaging device 11, the joint between the imaging device 11 and the cover glass 12, the joint between the imaging device 11 and the substrate 13, and the joint between the substrate and the signal cables 15. A proximal end part of the resin seal 17 has a shape of a four-sided pyramid, that is, a taper shape whose diameter reduces toward a proximal end of the proximal end part of the resin seal 17. The assembly cable extends from the apex of the four-sided pyramid of the proximal end part of the resin seal 17.

The frame 30 has a through hole 31 penetrating in the direction of an optical axis of the optical unit 10 and holds the imaging module 20 with the imaging module 20 being inserted into the through hole 31 from an insertion port 32 of a proximal end part of the frame 30. An observation window 33 in which the optical unit 10 is fitted is formed at a distal end part of the frame 30. When the imaging module 20 is inserted into the frame 30, a proximal end of the proximal end part of the resin seal 17 is arranged on a plane that includes a proximal end of the proximal end of the frame 30, that is, the insertion port 32 and that is orthogonal to the optical axis of the optical unit 10 or is arranged in the through hole 31 of the frame 30.

The first adhesive 41 adheres the outer circumference of the resin seal 17 on the proximal end side and an inner-circumferential surface of the insertion port 32 of the frame 30. As illustrated in FIG. 1B, the first adhesive 41 adheres the top and bottom surfaces of a taper surface 17a of the resin seal 17 and the inner circumferential surface of the insertion port 32 of the frame 30. From a viewpoint of prevention of a positional shift of the imaging module 20, the first adhesive 41 is preferably provided symmetrically, for example, on the top and bottom surfaces of the taper surface 17a or the right and left surfaces of the taper surface 17a; however, as long as the first adhesive 41 is arranged for the purpose of adhering part of the outer circumference of the resin seal 17 on the proximal end side and part of the inner circumferential surface of the insertion port 32 of the frame 30, even adhering and fixing in a single area achieves the effect of prevention of a positional shift. From a viewpoint that the first adhesive 41 cures immediately and temporarily fixes the inner circumference of the frame 30 and the resin seal 17, it is preferable that an ultraviolet cure adhesive be used.

The first adhesive 41 is supplied to the gap between the resin seal 17 and the frame 30 in order to adhere the resin seal 17 and the inner circumferential surface of the frame 30 and, from a viewpoint of prevention of dripping of the first adhesive 41, it is preferable that the first adhesive 41 (before curing) have a high viscosity.

The second adhesive 42 is supplied to the gap between the inner circumferential surface of the frame 30 at a position in which the through hole 31 is formed and the imaging module 20 that is inserted into the frame 30, thereby adhering the frame 30 and the imaging module 20 to each other. The second adhesive 42 is supplied into the through hole 31 from the insertion port 32 of the frame 30. In the first embodiment, the upper and lower sides of the insertion port 32 is blocked with the first adhesive 41 and the second adhesive 42 is thus supplied from the right and/or left side of the insertion port 32. It is preferable that a thermosetting resin be used as the second adhesive 42.

It is preferable that the second adhesive 42 (before curing) have a low viscosity from a viewpoint of easiness to supply the second adhesive 42 into the frame 30. It is preferable that the viscosity of the second adhesive 42 before curing be lower than that of the first adhesive 41 before curing.

It is preferable that the first adhesive 41 have a high hardness from a viewpoint of strength of temporal adhesion between the resin seal 17 and the inner circumferential surface of the frame 30 and of a positional accuracy. From a viewpoint of prevention of the imaging device 11 from being destroyed when a stress is applied to the endoscope distal end structure 100, it is preferable that a hardness of the second adhesive 42 after curing is low and is lower than that of the first adhesive 41 after curing.

Figure 3:
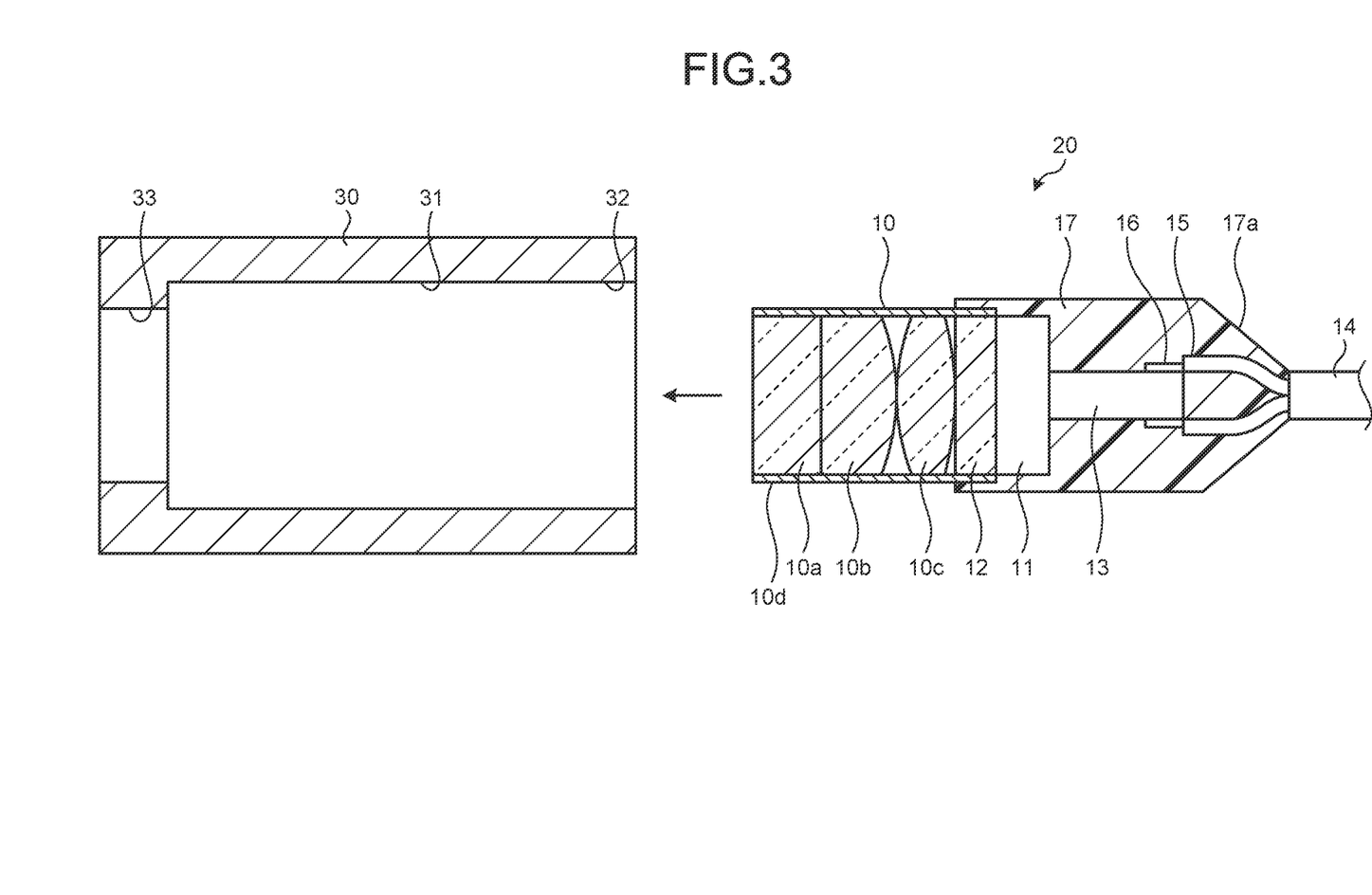
FIG. 3 is a diagram to explain a method of manufacturing the endoscope distal end structure in FIGS. 1A and 1B.
Figure 4A:
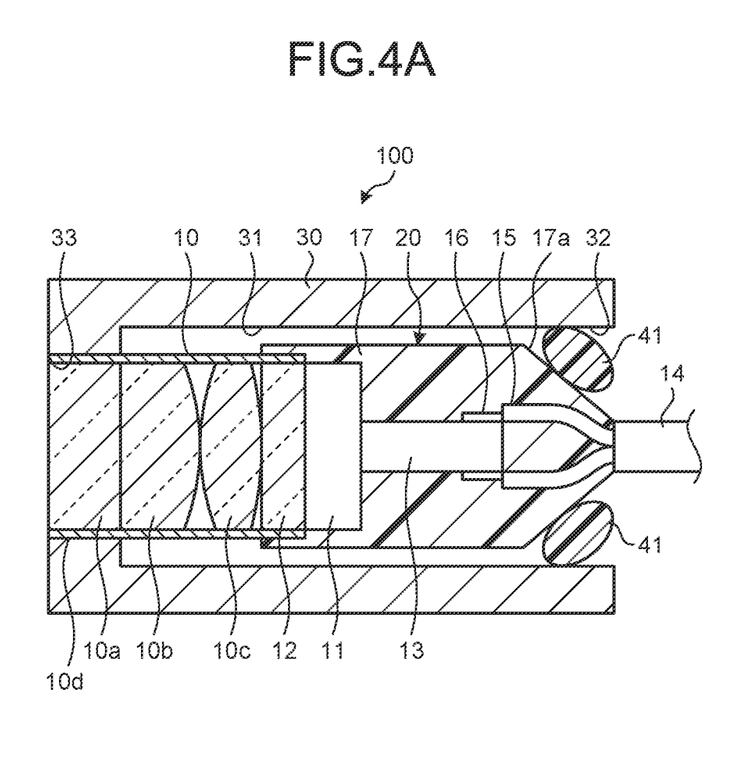
FIGS. 4A and 4B are a cross-sectional view and a back view, respectively, to explain the method of manufacturing the endoscope distal end structure in FIGS. 1A and 1B.
Figure 4B:
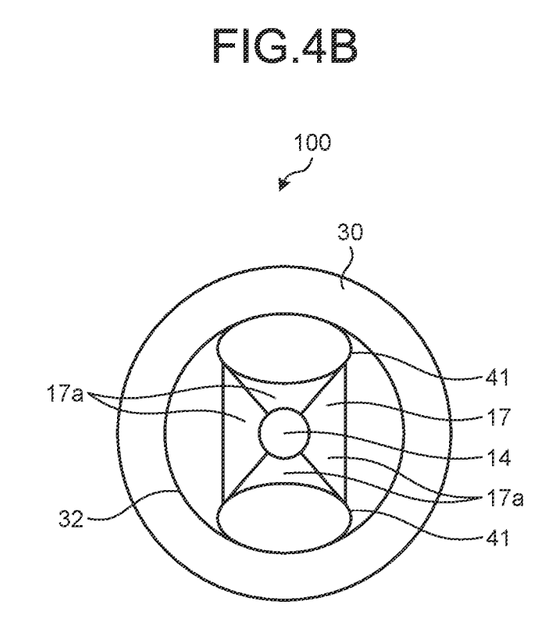

With reference to the drawings, a method of manufacturing the endoscope distal end structure 100 according to the first embodiment of the disclosure will be described. FIGS. 3, 4A, and 4B are diagrams to explain the method of manufacturing the endoscope distal end structure 100 in FIGS. 1A and 1B. FIG. 4A is a cross-sectional view and FIG. 4B is a back view.

As illustrated in FIG. 3, the imaging module 20 is inserted from the insertion port 32 into the through hole 31 of the frame 30. Inserting the optical unit 10 into the observation window 33 enables an alignment in the direction orthogonal to the optical-axis direction and alignment of a distal end surface of the optical unit 10 and a distal end surface of the frame 30, thereby enabling positioning in the optical-axis direction. After the positioning, as illustrated in FIGS. 4A and 4B, the first adhesive 41 is supplied to the taper surface 17a of the resin seal 17 and is caused to cure to temporarily fix the frame 30 and the imaging module 20. After the temporal fixing, the second adhesive 42 is supplied from the insertion port 32 into the frame 30 and is caused to cure to make it possible to manufacture the endoscope distal end structure 100 without positional shift between the frame 30 and the imaging module 20.

In the first embodiment, because the inner circumferential surface of the insertion port 32 of the frame 30 and the resin seal 17 are adhered and fixed to each other with the first adhesive 41, it is possible to prevent a positional shift of the imaging module 20 even in thermal expansion or thermal contraction that is associated with curing of the second adhesive 42. The first adhesive 41 makes it possible to inhibit the second adhesive 42 that is supplied into the frame 30 from flowing out. Furthermore, because the first adhesive 41 is arranged on the taper surface 17a of the resin seal 17, it is possible to increase the strength of the joint because of an increase in the area of the joint between the first adhesive 41 and the taper surface 17a of the resin seal 17 while preventing the first adhesive 41 from flowing out.

In the first embodiment, the endoscope distal end structure 100 that holds the imaging module 20 with the imaging module 20 being inserted into the through hole 31 of the frame 30 has been described and, in the case where an incorporated part of the endoscope (for example, a forceps cannel or a light guide) other than the imaging module is held with the frame, the same effect as that of the first embodiment can be achieved.

In the first embodiment, the taper surface 17a is formed on the proximal end side of the resin seal 17 and, from a viewpoint of prevention of a positional shift of the imaging module 20, it is not necessarily required to form the taper surface 17a. It is preferable to form the taper surface 17a because the taper surface 17a functions as a reservoir for the first adhesive 41 and is useful to increase the strength of the joint because of an increase in the area of the joint and prevent leakage of the first adhesive 41. The structure is not limited to the taper surface 17a as long as the structure has the above-described function. For example, when there is a structure that a distance R1 between the inner circumferential surface of the frame 30 and the outer circumference of the proximal end part of the resin seal 17 at a position in which the first adhesive 41 is arranged is longer than a distance R2 between the inner circumferential surface of the frame 30 and the outer circumference of the resin seal 17 at a position in which the second adhesive 42 is arranged, the gap between the inner circumferential surface of the proximal end part of the frame 30 and the outer circumference of the proximal end part of the resin seal 17 serves as a reservoir for the first adhesive 41 and it is possible to improve the joint strength and prevent leakage of the first adhesive 41.

Figure 5A:
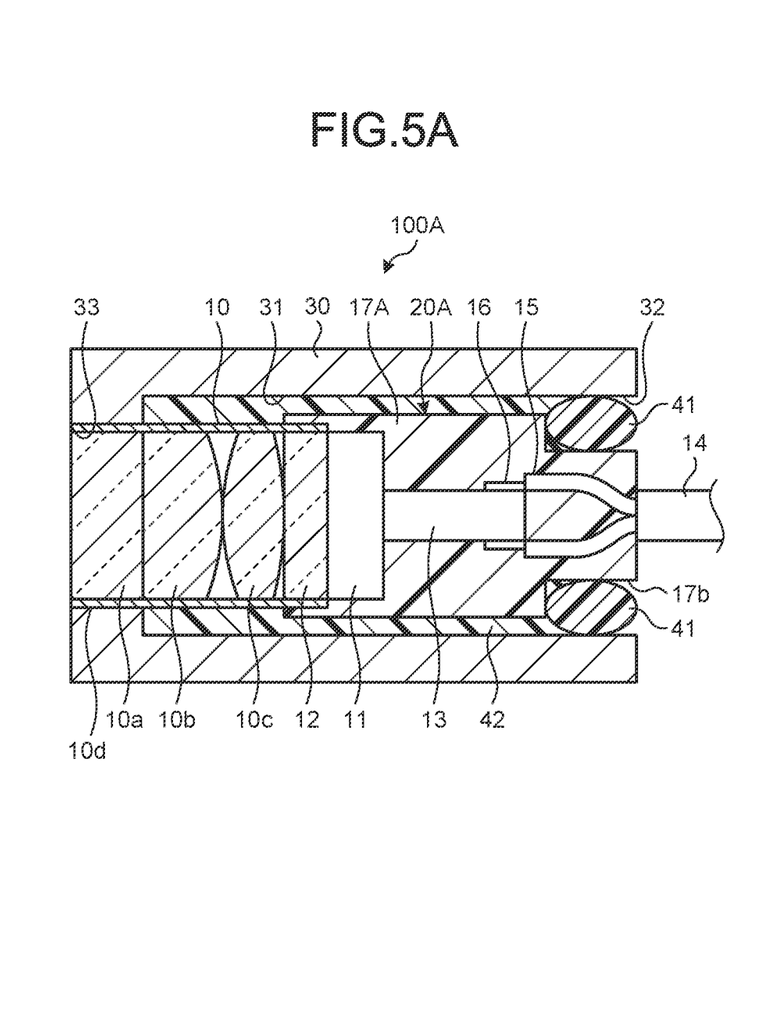
FIG. 5A is a cross-sectional view of an endoscope distal end structure according to Modification 1 of the first embodiment of the disclosure and FIG. 5B is a back view of the endoscope distal end structure according to the Modification 1 of the first embodiment of the disclosure.
Figure 5B:
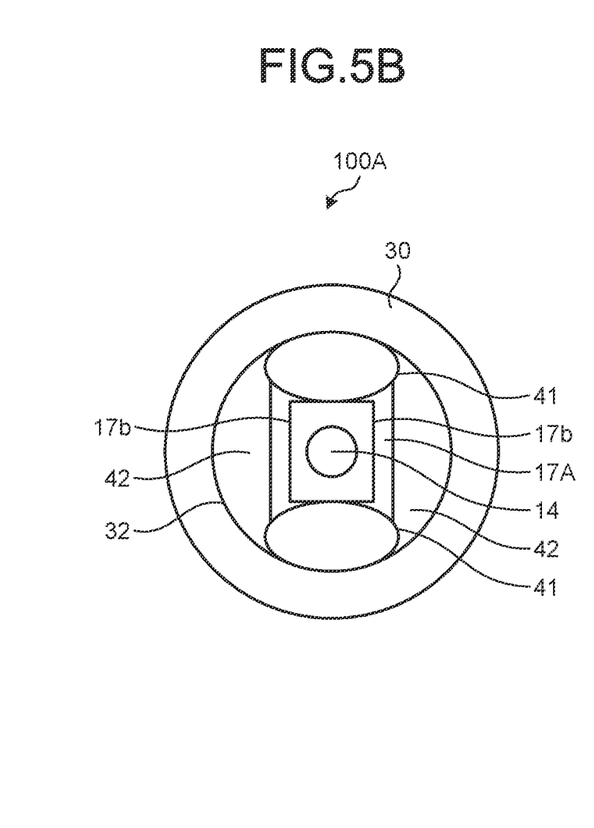

FIG. 5A is a cross-sectional view of an endoscope distal end structure 100A according to Modification 1 of the first embodiment of the disclosure and FIG. 5B is a back view of the endoscope distal end structure 100A. In the endoscope distal end structure 100A according to Modification 1 of the first embodiment, a resin seal 17A has a step 17b in the proximal end part instead of the taper surface 17a. In Modification 1, the step 17b is formed vertically and horizontally. Alternatively, the step may be formed in only the vertical direction in which the first adhesive 41 is arranged or only the horizontal direction in which the first adhesive 41 is arranged.

Figure 6A:
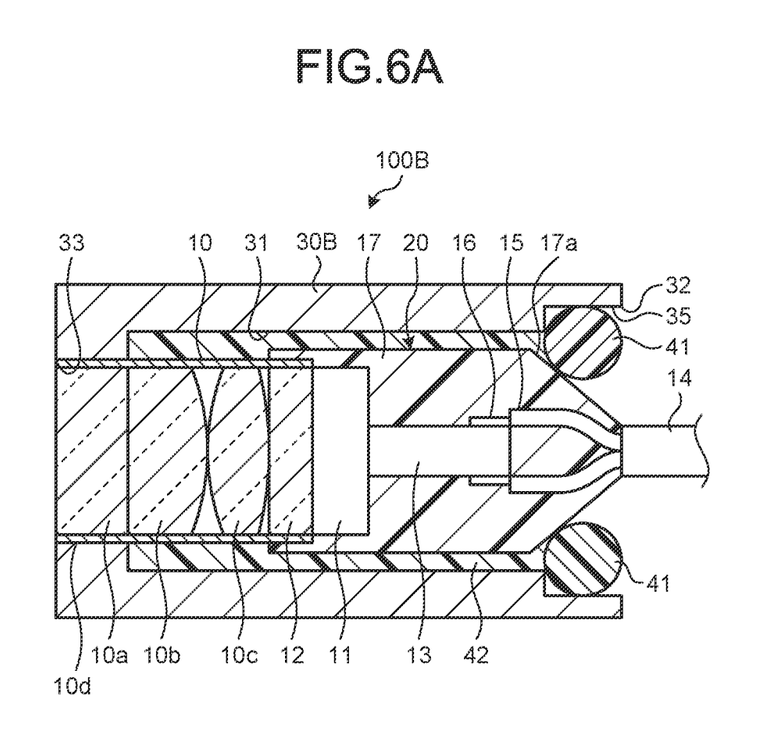
FIG. 6A is a cross-sectional view of an endoscope distal end structure according to Modification 2 of the first embodiment of the disclosure and FIG. 6B is a back view of the endoscope distal end structure according to the Modification 2 of the first embodiment of the disclosure.
Figure 6B:
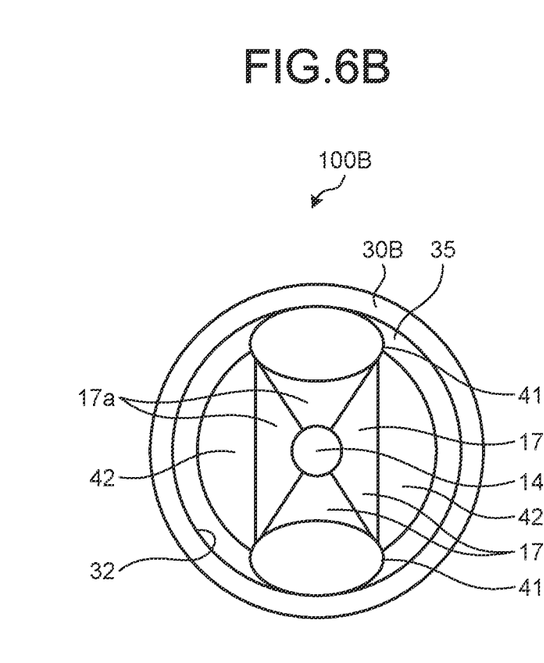

The step may be formed not in the resin seal but in the frame. FIG. 6A is a cross-sectional view of an endoscope distal end structure 100B according to Modification 2 of the first embodiment of the disclosure and FIG. 6B is a back view of the endoscope distal end structure 100B. In the endoscope distal end structure 100B according to Modification 2 of the first embodiment, a step 35 is formed in the insertion port 32 of a frame 30B. In modification 2, the taper surface 17a is formed in the proximal end part of the resin seal 17. Even without formation of the taper surface 17a, forming the step 35 in the frame 30B makes it possible to increase the joint strength and prevent the first adhesive 41 from leaking out.

Figure 7:
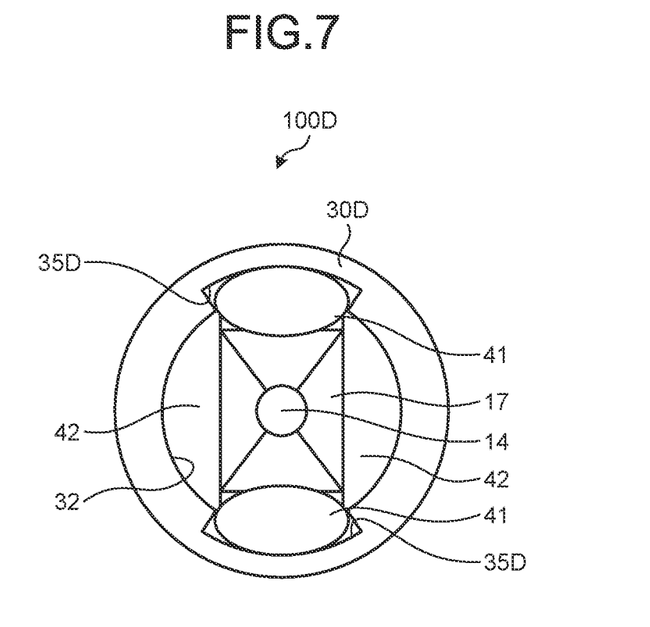
FIG. 7 is a back view of an endoscope distal end structure according to Modification 3 of the first embodiment of the disclosure.

Furthermore, in Modification 2, the step 35 is formed around the circumference of the insertion port 32. Alternatively, as illustrated in FIG. 7, a step 35D may be formed in the insertion port 32 of a frame 30D only in the vertical direction in which the first adhesive 41 is arranged. FIG. 7 is a back view of an endoscope distal end structure according to Modification 3 of the first embodiment of the disclosure.

Second Embodiment

Figure 8A:
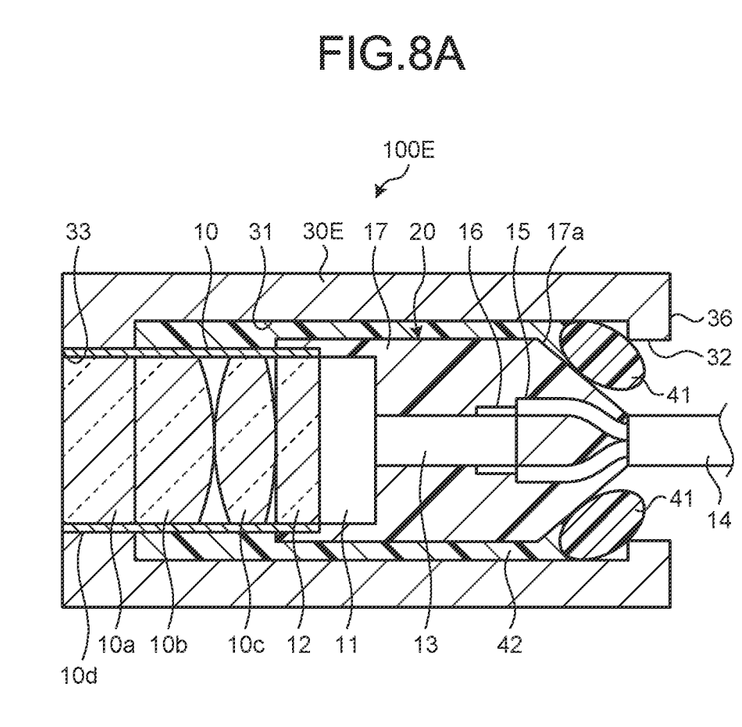
FIG. 8A is a cross-sectional view of an endoscope distal end structure according to a second embodiment of the disclosure and FIG. 8B is a back view of the endoscope distal end structure according to the second embodiment of the disclosure.
Figure 8B:
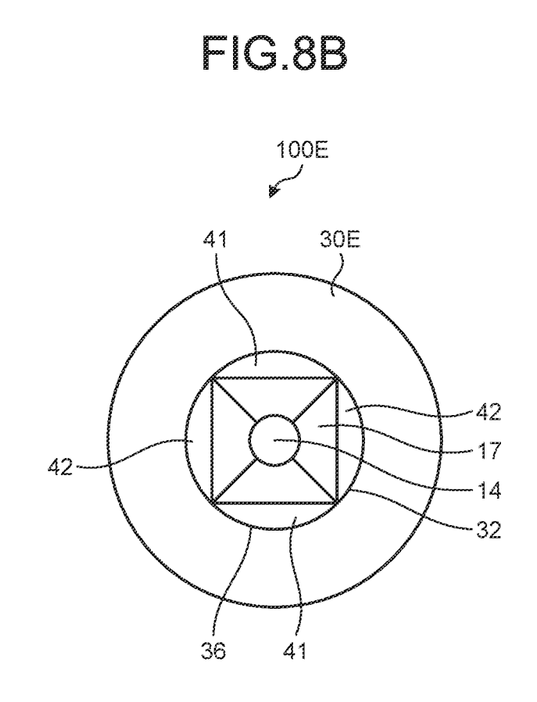

In a second embodiment, an endoscope distal end structure 100E has a protrusion 36 in the insertion port 32 of a frame 30E. FIG. 8A is a cross-sectional view of the endoscope distal end structure according to the second embodiment of the disclosure and FIG. 8B is a back view of the endoscope distal end structure.

The endoscope distal end structure 100E has the protrusion 36 that protrudes in the direction toward the center of the insertion port 32 in the insertion port 32 of the frame 30E. Forming the protrusion 36 in the insertion port 32 makes it possible to reduce flowing out of the first adhesive 41.

Figure 9:
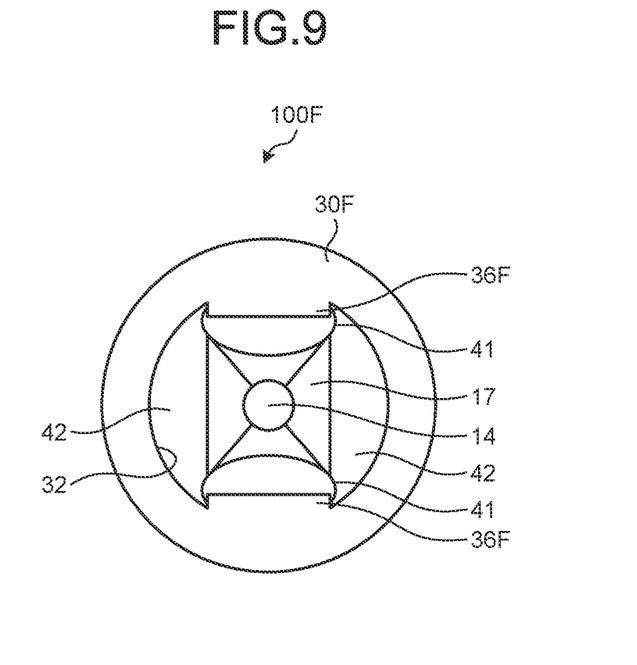
FIG. 9 is a back view of an endoscope distal end structure according to Modification 1 of the second embodiment of the disclosure.

In the second embodiment, the protrusion 36 is formed around the whole circumference of the insertion port 32. Alternatively, as illustrated in FIG. 9, a protrusion 36F may be formed only in the vertical direction in which the first adhesive 41 is arranged. FIG. 9 is a back view of an endoscope distal end structure 100F according to Modification 1 of the second embodiment of the disclosure.

Third Embodiment

Figure 10:
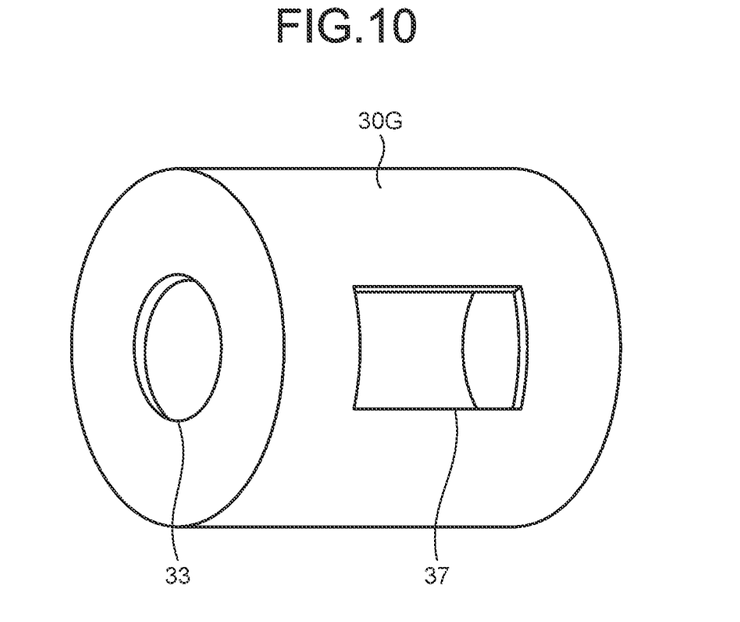
FIG. 10 is a perspective view of a frame according to a third embodiment of the disclosure.
Figure 11:
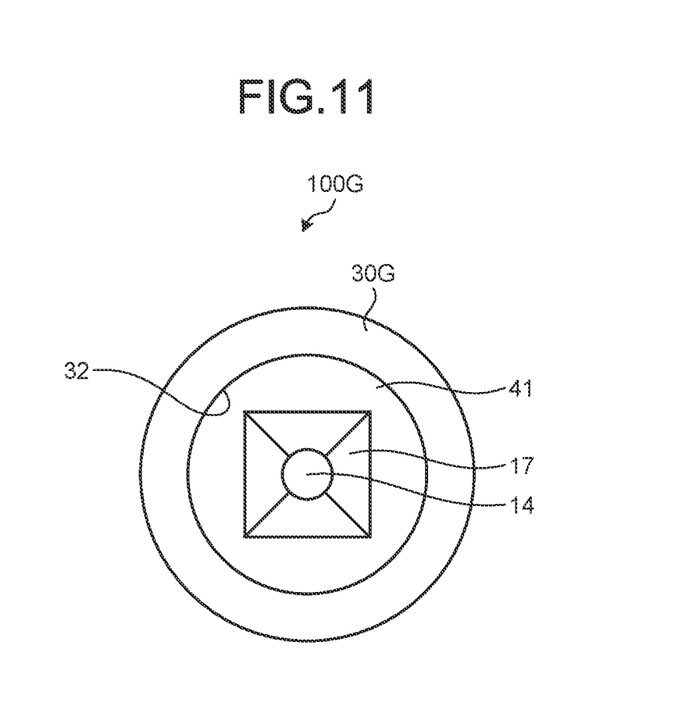
FIG. 11 is a back view of an endoscope distal end structure of the third embodiment of the disclosure.

In a third embodiment, an opening 37 from which the second adhesive 42 is injected is on a side surface of a frame 30G. FIG. 10 is a perspective view of the frame 30G according to a third embodiment of the disclosure. FIG. 11 is a back view of an endoscope distal end structure 100G of the third embodiment of the disclosure.

In the endoscope distal end structure 100G, the frame 30G has the opening 37 from which the second adhesive 42 is injected on a side surface parallel to the optical axis direction. As illustrated in FIG. 11, the first adhesive 41 adheres the outer circumference of the resin seal 17 on the proximal end side and the inner circumferential surface of the insertion port 32 of the frame 30G along the whole circumference. In the third embodiment, because the first adhesive 41 is arranged in the gap between the frame 30G on the side of the insertion port 32 and the resin seal 17 along the whole circumference, it is possible to more assuredly prevent the second adhesive 42 from flowing out of the insertion port 32.

Figure 12:
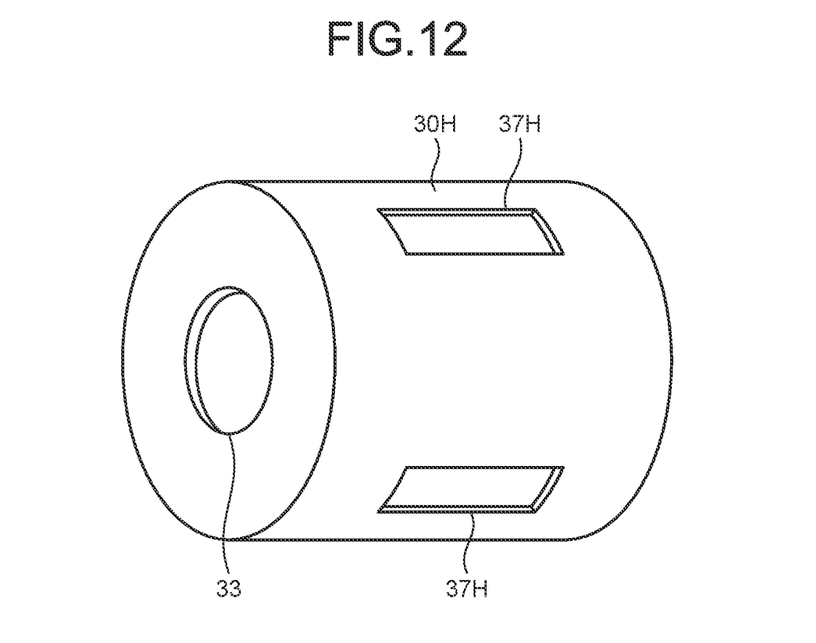
FIG. 12 is a perspective view of a frame according to Modification 1 of the third embodiment of the disclosure.

In the third embodiment, the single opening 37 is formed in the frame 30G; however, the opening is not limited to this. As illustrated in FIG. 12, two openings 37H may be formed. FIG. 12 is a perspective view of a frame 30H according to Modification 1 of the third embodiment of the disclosure. Forming the two openings 37H makes it possible to easily supply the second adhesive 42.

According to the disclosure, it is possible to prevent a positional shift of the imaging module in the frame and, even when an adhesive with a low viscosity is used as an adhesive that is supplied into the frame, inhibit the adhesive from flowing out.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope distal end structure comprising:
an imaging module configured to form an image of a subject using an optical unit, generate an image signal by performing photoelectric conversion on the formed image using an imaging device, and transmit the generated image signal using a cable;
a frame that has a through hole penetrating in a direction of an optical axis of the optical unit, the frame being configured to hold the imaging module with the imaging module being inserted into the through hole from an insertion port that is formed in a proximal end part of the frame;
a first adhesive that is arranged in a gap between an outer circumference of a proximal end part of a resin seal and an inner circumferential surface of the frame on a side of the insertion port to adhere at least part of the outer circumference of the proximal end part of the resin seal and at least part of the inner circumferential surface of the frame, the resin seal sealing at least from a proximal end of a side surface part of the optical unit to a joint of the cable; and
a second adhesive that is arranged in a gap between the inner circumferential surface of the frame at a position in which the through hole is formed and the imaging module that is inserted into the through hole to adhere the frame and the imaging module to each other.

2. The endoscope distal end structure according to claim 1, wherein a distance between the inner circumferential surface of the frame and the outer circumference of the resin seal at a position in which the first adhesive is arranged is longer than a distance between the inner circumferential surface of the frame and the outer circumference of the resin seal at a position in which the second adhesive is arranged.

3. The endoscope distal end structure according to claim 2, wherein the proximal end part of the resin seal has a taper shape whose diameter reduces.

4. The endoscope distal end structure according to claim 1, wherein a proximal end of the proximal end part of the resin seal is arranged on a plane that includes a proximal end of the a proximal end part of the frame and that is orthogonal to the optical axis of the optical unit or is arranged in the through hole of the frame.

5. The endoscope distal end structure according to claim 1, further comprising a protrusion at the insertion port of the frame, the protrusion protruding in a direction toward a center of the insertion port.

6. The endoscope distal end structure according to claim 1, wherein the second adhesive after curing has a hardness lower than a hardness of the first adhesive after curing.

7. The endoscope distal end structure according to claim 1, wherein the first adhesive before curing has a viscosity higher than that of the second adhesive.

8. The endoscope distal end structure according to claim 1, wherein the first adhesive is an ultraviolet cure adhesive and the second adhesive is a thermosetting adhesive.

9. The endoscope distal end structure according to claim 1, wherein
the frame has a side surface parallel to the direction of the optical axis, and
the side surface of the frame includes an opening from which the second adhesive is injected.

10. An endoscope comprising the endoscope distal end structure according to claim 1.

* * * * *